United States Patent
Lee et al.

(10) Patent No.: US 10,372,160 B2
(45) Date of Patent: Aug. 6, 2019

(54) RING SHAPED WEARABLE DEVICE HAVING PROJECTOR

(71) Applicant: LG ELECTRONICS INC., Seoul (KR)

(72) Inventors: Byunghwa Lee, Seoul (KR); Choonghwan Shin, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 15/525,834

(22) PCT Filed: Nov. 14, 2014

(86) PCT No.: PCT/KR2014/010954
§ 371 (c)(1),
(2) Date: May 10, 2017

(87) PCT Pub. No.: WO2016/076461
PCT Pub. Date: May 19, 2016

(65) Prior Publication Data
US 2017/0319134 A1 Nov. 9, 2017

(30) Foreign Application Priority Data
Nov. 10, 2014 (KR) .................. 10-2014-0155565

(51) Int. Cl.
*G06F 1/16* (2006.01)
*G03B 21/28* (2006.01)
(Continued)

(52) U.S. Cl.
CPC ............ *G06F 1/163* (2013.01); *A61B 5/6831* (2013.01); *G03B 21/14* (2013.01); *G03B 21/147* (2013.01);
(Continued)

(58) Field of Classification Search
CPC ........ G03B 21/14; G03B 21/28; G03B 29/00; H04N 9/3188; H04N 9/3194;
(Continued)

(56) References Cited

U.S. PATENT DOCUMENTS

| 6,035,035 | A * | 3/2000 | Firooz | H04B 1/385 |
| | | | | 379/433.1 |
| 6,371,616 | B1 * | 4/2002 | Doany | G09G 3/002 |
| | | | | 348/E5.139 |

(Continued)

FOREIGN PATENT DOCUMENTS

| JP | 3060269 U | 8/1999 |
| KR | 10-2001-0051469 A | 6/2001 |

(Continued)

*Primary Examiner* — Bao-Luan Q Le
(74) *Attorney, Agent, or Firm* — Birch, Stewart, Kolasch & Birch, LLP

(57) ABSTRACT

A wearable device, which comprises: a ring-shaped case having an opening part formed in the middle thereof; a projector mounted at one side of the case and outputting an image; a lens part adjusting the direction and the size of the image, which is projected from the projector, so as to project the image; and a control unit for adjusting the projector and the lens part according to an image signal, can deliver visual information to a user wearing the wearable device even without a separate display unit by outputting the image onto the hand of the user.

16 Claims, 7 Drawing Sheets

(51) Int. Cl.
*H04N 9/31* (2006.01)
*G04G 17/04* (2006.01)
*G03B 21/14* (2006.01)
*A61B 5/00* (2006.01)
*G06F 3/01* (2006.01)
*G03B 17/54* (2006.01)

(52) U.S. Cl.
CPC ............. *G03B 21/28* (2013.01); *G04G 17/04* (2013.01); *G06F 3/014* (2013.01); *G06F 3/017* (2013.01); *H04N 9/3185* (2013.01); *H04N 9/3188* (2013.01); *H04N 9/3194* (2013.01); *G03B 17/54* (2013.01)

(58) Field of Classification Search
CPC .... H04N 9/3185; H04N 9/3182; G06F 3/017; G06F 1/163; G06F 3/014
See application file for complete search history.

(56) References Cited

U.S. PATENT DOCUMENTS

| | | | | |
|---|---|---|---|---|
| 7,213,926 B2* | 5/2007 | May | ...................... | H04N 5/74 348/E5.137 |
| 7,284,866 B2* | 10/2007 | Buchmann | ......... | G02B 26/0816 353/121 |
| 7,871,167 B2* | 1/2011 | Amano | .................. | G03B 21/28 353/70 |
| 8,292,438 B2* | 10/2012 | Nishikawa | ........... | H04N 9/3105 353/101 |
| 8,558,937 B2* | 10/2013 | Park | ...................... | G03B 17/54 348/333.06 |
| 8,774,861 B1 | 7/2014 | Cathey | | |
| 9,069,164 B2* | 6/2015 | Starner | ................ | G02B 27/017 |
| 9,372,096 B2* | 6/2016 | Maezawa | ................ | G01C 22/00 |
| 9,846,529 B2* | 12/2017 | Brehmer | ............. | G06F 3/04842 |
| 9,872,002 B2* | 1/2018 | Zhao | ...................... | H04N 9/3173 |
| 10,061,387 B2* | 8/2018 | Toney | ....................... | G06F 3/017 |
| 2004/0222301 A1* | 11/2004 | Willins | ................ | G02B 26/105 235/472.01 |
| 2006/0103811 A1* | 5/2006 | May | ........................ | H04N 5/74 353/69 |
| 2006/0146015 A1* | 7/2006 | Buchmann | ......... | G02B 26/0816 345/156 |
| 2009/0040473 A1* | 2/2009 | Amano | .................. | G03B 21/28 353/70 |
| 2009/0051832 A1 | 2/2009 | Banks et al. | | |
| 2010/0128234 A1* | 5/2010 | Nishikawa | ........... | H04N 9/3105 353/98 |
| 2012/0154663 A1* | 6/2012 | Park | ...................... | G03B 17/54 348/333.06 |
| 2012/0249409 A1* | 10/2012 | Toney | ..................... | G06F 3/017 345/156 |
| 2013/0016070 A1* | 1/2013 | Starner | ................ | G02B 27/017 345/175 |
| 2014/0046588 A1* | 2/2014 | Maezawa | ................ | G01C 22/00 701/487 |
| 2014/0055352 A1 | 2/2014 | Davis et al. | | |
| 2014/0078694 A1* | 3/2014 | Wissmar | ................ | G04G 17/04 361/749 |
| 2015/0242094 A1* | 8/2015 | Brehmer | ............... | G06F 3/0488 715/765 |
| 2015/0323998 A1* | 11/2015 | Kudekar | ................ | G06F 1/163 345/156 |
| 2016/0301906 A1* | 10/2016 | Zhao | .................... | H04N 9/3173 |

FOREIGN PATENT DOCUMENTS

| | | |
|---|---|---|
| KR | 10-2009-0061179 A | 6/2009 |
| WO | WO 2008/115689 A1 | 9/2008 |
| WO | WO 2016/036017 A1 | 3/2016 |

\* cited by examiner

RING SHAPED WEARABLE DEVICE HAVING PROJECTOR

CROSS REFERENCE TO RELATED APPLICATIONS

This application is the National Phase of PCT International Application No. PCT/KR2014/010954, filed on Nov. 14, 2014, which claims priority under 35 U.S.C. 119(a) to Patent Application No. 10-2014-0155565, filed in the Republic of Korea on Nov. 10, 2014, all of which are hereby expressly incorporated by reference into the present application in their entireties.

TECHNICAL FIELD

The present invention relates to a wearable device which is wearable on a wrist of a user.

BACKGROUND ART

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As such functions become more diversified, the mobile terminal can support more complicated functions such as capturing images or video, reproducing music or video files, playing games, receiving broadcast signals, and the like. By comprehensively and collectively implementing such functions, the mobile terminal may be embodied in the form of a multimedia player or device.

Meanwhile, the mobile terminal may be extended to a wearable device that may be wearable on a body of a user in addition to a mobile device that may be used by a user by holding it in the user's hand. Examples of the wearable device include a smart watch, smart glasses, a head mounted display (HMD), etc.

However, since convenience in wearing is important in the wearable device, the wearable device has a limitation in its size. Therefore, it is required to reduce a size of parts installed in a wearable terminal. Particularly, since a display unit requires a large area for visibility, a problem occurs in that it is difficult to install the display unit on the wearable terminal.

DISCLOSURE

Technical Problem

An object of the present invention is to provide a wearable device that includes a projector for outputting an image to a hand of a user who wears the wearable device.

Technical Solution

A wearable device is provided, which comprises a ring-shaped case having an opening at the center thereof; a projector packaged in one side of the case, outputting an image; a lens module adjusting a direction and a size of the image, which is projected from the projector, so as to project the image; and a controller adjusting the projector and the lens module in accordance with an image signal.

A wrist of a user is inserted to the opening of the case and the projector projects the image toward a hand of the user, and the wearable device further comprises a sensor for sensing a bent angle of the user's wrist, wherein the controller may control the image projected from the projector to reduce distortion of the image displayed on the hand of the user by separately adjusting a size of an image displayed on a portion close to the user's wrist and a size of an image displayed on a portion far away from the user's wrist.

The wrist of a user is inserted to the opening of the case and the projector projects the image toward a hand of the user, and the wearable device further comprises a sensor for sensing a bent angle of the user's wrist, wherein the controller may adjust a direction and size toward which the lens module projects the image, in accordance with the bent angle of the user's wrist.

The wrist of a user is inserted to the opening of the case and the projector projects the image toward a hand of the user, and the wearable device further comprises a sensor for sensing a bent angle of the user's wrist, wherein the controller may control the image projected from the projector to be changed in accordance with the bent angle of the user's wrist.

The sensor may be at least one of a myoelectric sensor and a proximity sensor.

The lens module may be configured such that the image of the projector is incident at one side and projected toward a front.

The lens module may include a first reflective plate for reflecting the image incident at one side toward the outside of the ring, and a second reflective plate for reflecting the image reflected by the first reflective plate toward a front direction.

The lens module may further include a first lens for reducing the image incident at one side and delivering the reduced image to the first reflective plate, and a second lens arranged between the first reflective plate and the second reflective plate, magnifying the image reflected by the first reflective plate and delivering the magnified image to the second reflective plate.

The controller may adjust an inclined angle of the second reflective plate.

The case is partially made of a flexible material, and the wearable device further comprises an elastic member arranged at one side of a continuous surface of the ring to be spaced apart from the projector, adjusting a size of the ring in accordance with its variable length.

The wearable device may further comprise a frame on which the projector is mounted; a main board fixed to the frame; a camera arranged to be spaced apart from the projector; and a flexible substrate connecting the camera with the main board.

The wearable device may further comprise a battery arranged inside the case, including a curve and having one side inserted to the frame, wherein the frame may further include a battery holder including a curve corresponding to a shape of one side of the battery.

The wearable device may further comprise a wireless communication unit packaged in the case, receiving an image signal from an external terminal.

Advantageous Effects

According to at least one of the embodiments of the present invention, it is possible to deliver visual information to a user who wears a wearable device by outputting an image to a hand of the user even though a separate display unit is not provided in the wearable device.

Also, since the wearable device is not provided with a display unit, its size may be reduced.

Also, it is possible to provide an image of which distortion is minimized, by controlling the image in accordance with a bent angle of a wrist of a user.

Additional scope of applicability of the present invention will be apparent from the following detailed description. However, since various modifications and corrections may explicitly be understood by persons skilled in the art within spirits and scope of the present invention, the detailed description and a specific embodiment such as the preferred embodiment of the present invention should be understood to be only given as an example.

BEST MODE FOR CARRYING OUT THE INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present.

A singular representation may include a plural representation unless it represents a definitely different meaning from the context.

In this application, it is to be understood that the terms such as "include" and "has" are intended to designate that features, numbers, steps, operations, elements, parts, or their combination, which are disclosed in the specification, exist, and are intended not to previously exclude the presence or optional possibility of one or more other features, numbers, steps, operations, elements, parts, or their combinations.

Figure 1:
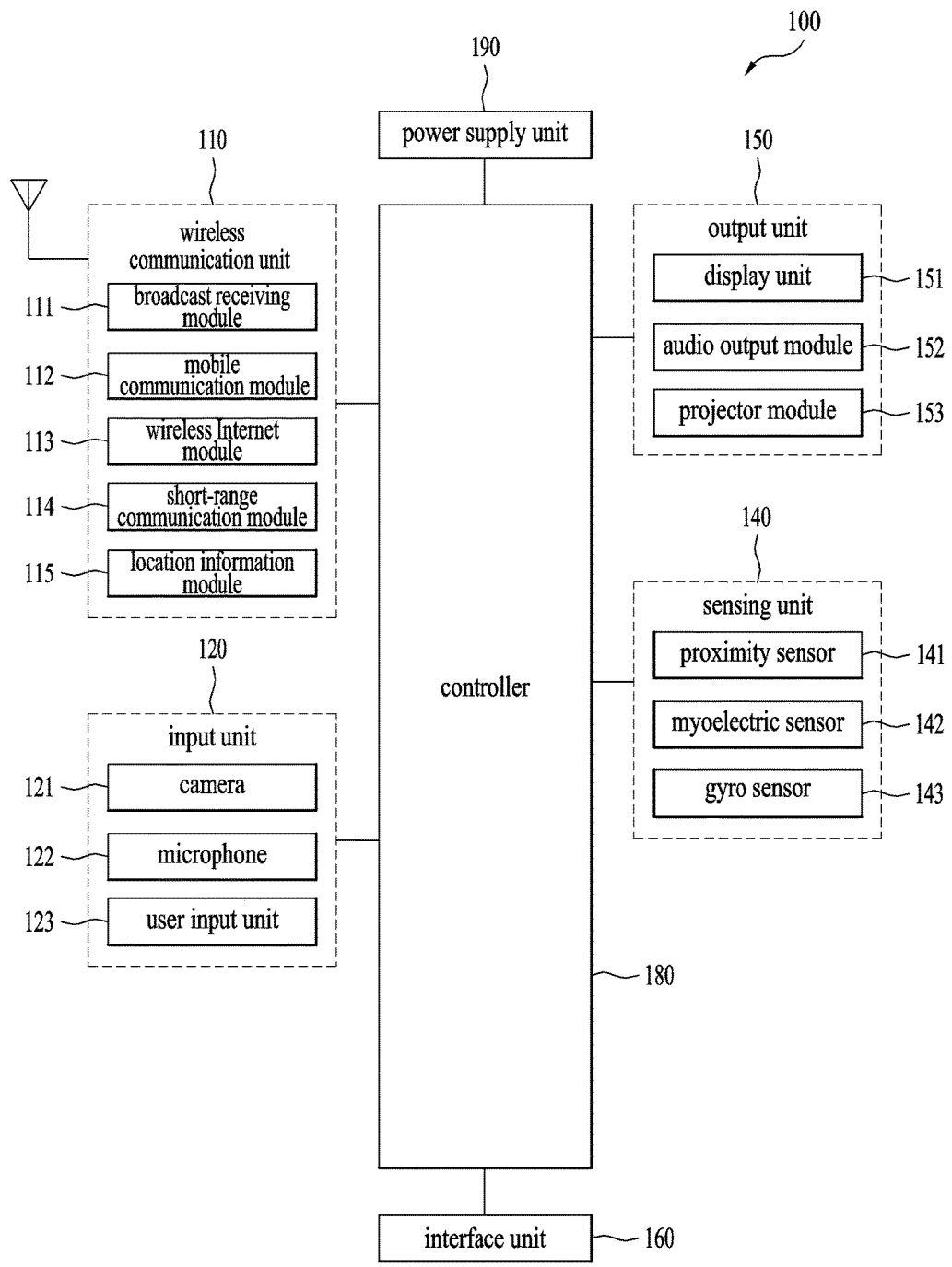
FIG. 1 is a block diagram of a wearable device according to the present invention.

FIG. 1 is a block diagram of a wearable device according to the present invention.

The wearable device 100 may include a wireless communication unit 110, an input unit 120, a sensing unit 140, an output unit 150, an interface unit 160, a memory 170, a controller 180, and a power supply unit 190. It is understood that implementing all of the illustrated components in FIG. 1A is not a requirement, and that greater or fewer components may alternatively be implemented.

In more detail, the wireless communication unit 110 may include one or more modules which permit communications such as wireless communications between the wearable device 100 and a wireless communication system, communications between the wearable device 100 and another wearable device 100, or communications between the wearable device 100 and an external server. Further, the wireless communication unit 110 may include one or more modules which connect the wearable device 100 to one or more networks.

The wireless communication unit 110 may include at least one of a broadcast receiving module 111, a mobile communication module 112, a wireless Internet module 113, a short-range communication module 114, and a location information module 115.

The input unit 120 may include a camera 121 or video input unit for video signal input, a microphone 122 or audio input unit for audio signal input, and a user input unit 123 (for example, a touch key, a push key, a mechanical key, and the like) for allowing a user to input information. Audio data or image data obtained by the input unit 120 may be analyzed and processed by a control command of a user.

The sensing unit 140 may include one or more sensors configured to sense at least one of internal information of the wearable device, the surrounding environment of the wearable device, and user information. For example, the sensing unit 140 may include at least one of a proximity sensor 141, an illumination sensor 142, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, etc.), and a chemical sensor (for example, an electronic nose, a health care sensor, a biometric sensor, and the like). Meanwhile, the wearable device disclosed in this specification may be configured to utilize information sensed from at least two or more of the sensors.

The output unit 150 is configured to output various types of outputs related to audio, video, tactile output, and the like. The output unit 150 may include at least one of a display unit 151, an audio output module 152, and a projector module 153.

The display unit 151 may have an inter-layered structure or an integrated structure with a touch sensor in order to facilitate a touch screen. The touch screen may provide an output interface between the wearable device 100 and a user, as well as function as the user input unit 123 which provides an input interface between the wearable device 100 and the user.

The projector module 153 is an output device that delivers visual information to a user by ejecting light including an image without a screen of the device and outputting the image to an external screen.

The projector module 153 may be provided together with the display unit 151, or may only be provided on behalf of the display unit 151. Since the wearable device 100 cannot be formed at a large size considering its portability, the projector module 153 may be used to provide an image of a large sized screen even in spite of a small size of the wearable device.

The interface unit 160 serves as an interface with various types of external devices that can be coupled to the wearable device 100. The interface unit 160, for example, may include at least one of wired or wireless headset ports, external power supply ports, wired or wireless data ports, memory card ports, ports for connecting a device having an identification module, audio input/output (I/O) ports, video I/O ports, and earphone ports. In some cases, the wearable device 100 may perform assorted control functions associated with a connected external device, in response to the external device being connected to the interface unit 160.

Also, the memory 170 stores data to support various functions of the wearable device 100. The memory 170 may be configured to store a plurality of application programs or applications executed in the wearable device 100 and data or instructions for operations of the wearable device 100. Some of these application programs may be downloaded from an external server via wireless communication. Also, at least some of the application programs may be installed within the wearable device 100 at time of manufacturing or shipping, which is the case for basic functions of the wearable device 100 (for example, receiving a call, placing a call, receiving a message, sending a message, and the like). It is common for application programs to be stored in the memory 170, installed in the wearable device 100, and executed by the controller 180 to perform an operation (or function) for the wearable device 100.

The controller 180 typically functions to control overall operation of the wearable device 100, in addition to the operations associated with the application programs. The controller 180 may provide or process information or functions appropriate for a user by processing signals, data, information and the like, which are input or output by the aforementioned various components, or activating application programs stored in the memory 170.

Also, the controller 180 may control some or all of the components illustrated in FIG. 1A to execute the application programs stored in the memory 170. Moreover, the controller 180 may execute at least two or more of the components included in the wearable device 100 in combination to execute the application programs.

The power supply unit 190 is configured to receive external power or internal power in order to supply appropriate power required for operating elements and components included in the wearable device 100 under the control of the controller 180. The power supply unit 190 may include a battery, and the battery may be configured as an embedded type battery or an exchangeable type battery.

Some or more of the components may be operated cooperatively to embody an operation, control or a control method of the wearable device in accordance with various embodiments which will be described hereinafter. Also, the operation, control or control method of the wearable device may be realized on the wearable device by driving of one or more application problems stored in the memory 170.

Figure 2:
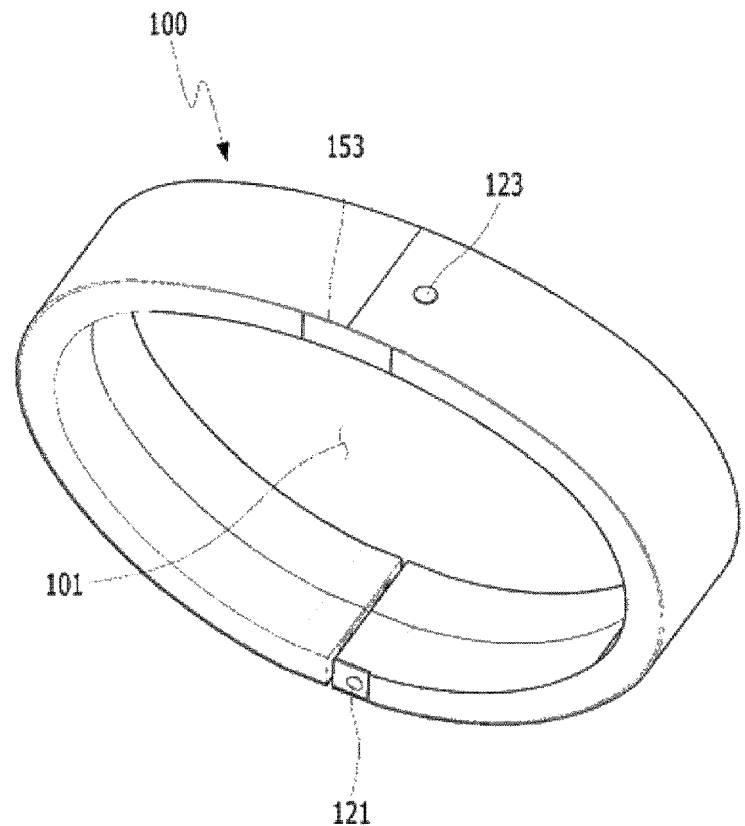
FIG. 2 is a perspective view illustrating one embodiment of a wearable device according to the present invention.
Figure 3:
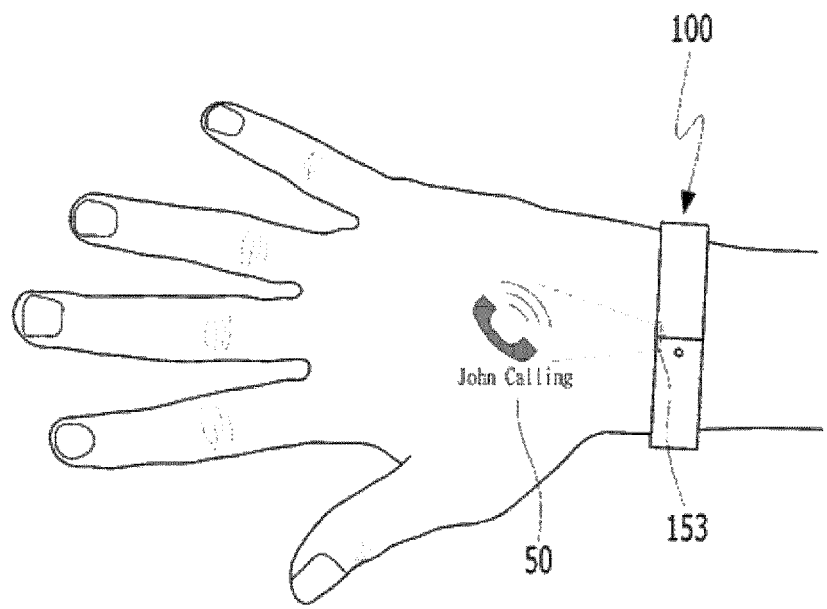
FIG. 3 is a view illustrating a usage example of a wearable device according to the present invention.

FIG. 2 is a perspective view illustrating one embodiment of a wearable device according to the present invention, and FIG. 3 is a view illustrating a usage example of a wearable device according to the present invention. Referring to FIG. 2, the wearable device 100 of the present invention is a ring shaped wearable device 100 used to be worn on a wrist of a user, and since the wearable device 100 includes a projector 1535, a display unit may be omitted.

The ring shaped wearable device 100 provided with an opening 105 at the center is configured in such a manner that a wrist of a user is inserted into the opening 105. The projector 1535, which projects an image 50 toward a direction in which the opening 105 is formed, allows the image 50 to be generated on a wrist or hand of a user who wears the wearable device as shown in FIG. 3.

Figure 4:
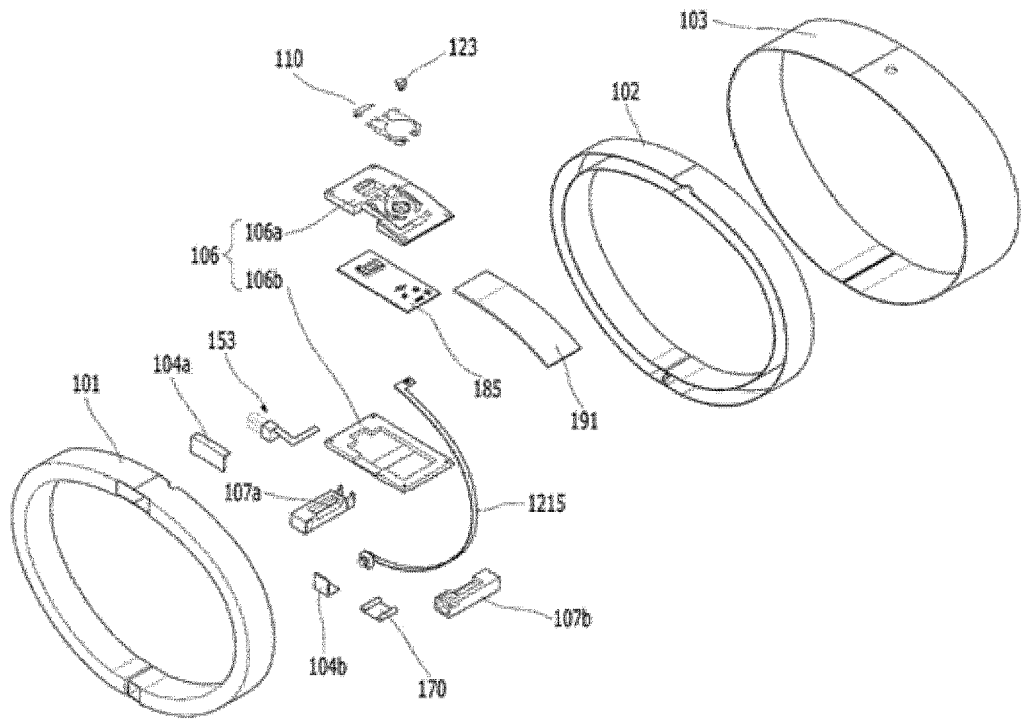
FIG. 4 is an exploded perspective view illustrating one embodiment of a wearable device according to the present invention.

FIG. 4 is an exploded perspective view illustrating one embodiment of a wearable device 100 according to the present invention. Referring to FIG. 4, cases 101 and 102, a deco cover 103 covering outsides of the cases 101 and 102, frames 106 and 107 in which components are packaged, a battery 191, a main board 185, a wireless communication unit 110 for performing wireless communication with an external device, a user input unit 123 exposed to the outsides of the cases 101 and 102, a projector module 153, a camera 121, and the like are packaged in the wearable device.

The cases 101 and 102 may be made of a hard material such as an injection molded material, may be made of a soft material such as silicon, or may partially include a hard material and a soft material. In case of the cases made of a hard material, it is convenient to package parts in the device and protect the parts. In case of the cases made of a soft material, it is easy for a user to wears the wearable device.

The cases 101 and 102 form a control box therein by coupling the first case 101, 102 with the second case 101, 102, and the frames 106 and 107, the battery 191 and the main board 185 are packaged inside the control box. The cases 101 and 102 are formed in a shape of ring, and include the opening 105 at the center.

Figure 5:
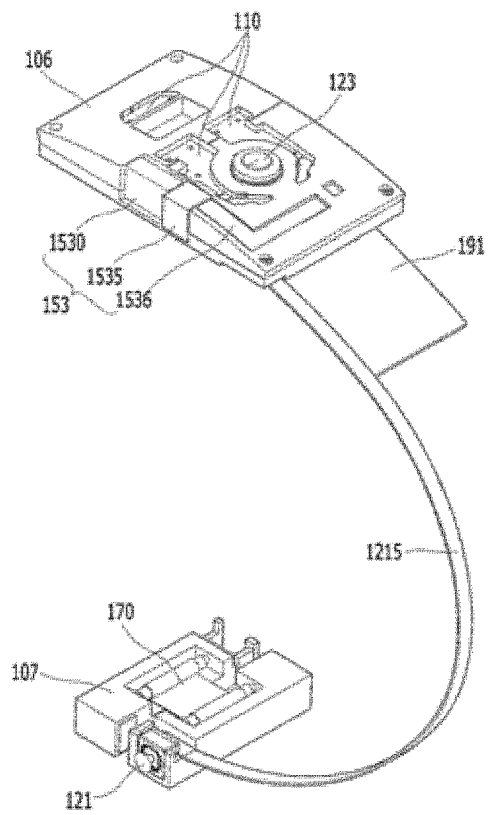
FIG. 5 is a view illustrating inner parts except a case of a wearable device according to the present invention.

FIG. 5 is a view illustrating inner parts except a case of a wearable device according to the present invention. A flexible substrate 1215 for connecting the first frame 106 with the second frame 107 is shown in FIG. 5.

The frames 106 and 107 are arranged inside the cases 101 and 102 to fix various parts which are fixed in the cases 101 and 102. Particularly, if the cases 101 and 102 are made of a soft material, the frames 106 and 107 add rigidity to the wearable device 100 to prevent the parts from being damaged, for example, when the cases 101 and 102 are bent.

The cases 101 and 102 corresponding to a portion where the frames 106 and 107 are arranged are made of a hard material, and the cases 101 and 102 corresponding to the other portion are made of a soft material, whereby it is possible to improve wearing of the wearable device while optimizing protection of the parts.

Only one frame may be provided, or several frames may be distributed in the ring of the cases 101 and 102. In this embodiment, two frames 106 and 107 may be used in such a manner that the parts are arranged to be divided by the first frame 106 and the second frame 107 to prevent a hard area from being widened due to increase of one frame size.

The projector module 153, the main board 185, the battery 191, the wireless communication unit 110, the user input unit 123, etc. may be packaged in the first frame 106 arranged at one side, while the camera 121 may be arranged in the second frame 107 spaced apart from the first frame 106. In addition, a microphone (not shown), an audio output unit (not shown), etc. may further be arranged in the first frame 106 or the second frame 107.

The flexible substrate 1215 is connected between the frames 106 and 107 to transmit and receive a signal. Since the flexible substrate 1215 may be bent, the soft portion of the cases 101 and 102 may be deformed without any damage when the soft portion is deformed.

The wireless communication unit 110 may include a plurality of antennas 110. A main antenna for mobile communication, a Bluetooth antenna for short-range wireless communication, a Wi-Fi antenna for wireless Internet, etc. may be packaged in the wearable device. The antenna 110 may be arranged outside the frames 106 and 107 to transmit and receive a signal without being interrupted from a body of a user.

The user input unit 123 may be exposed outside the cases 101 and 102 to allow a user to control ON/OFF of the wearable device 100 by using the user input unit 123 or input a command for controlling a specific function. Although one user input unit 123 is shown, a plurality of user input units may be provided.

Figure 6:
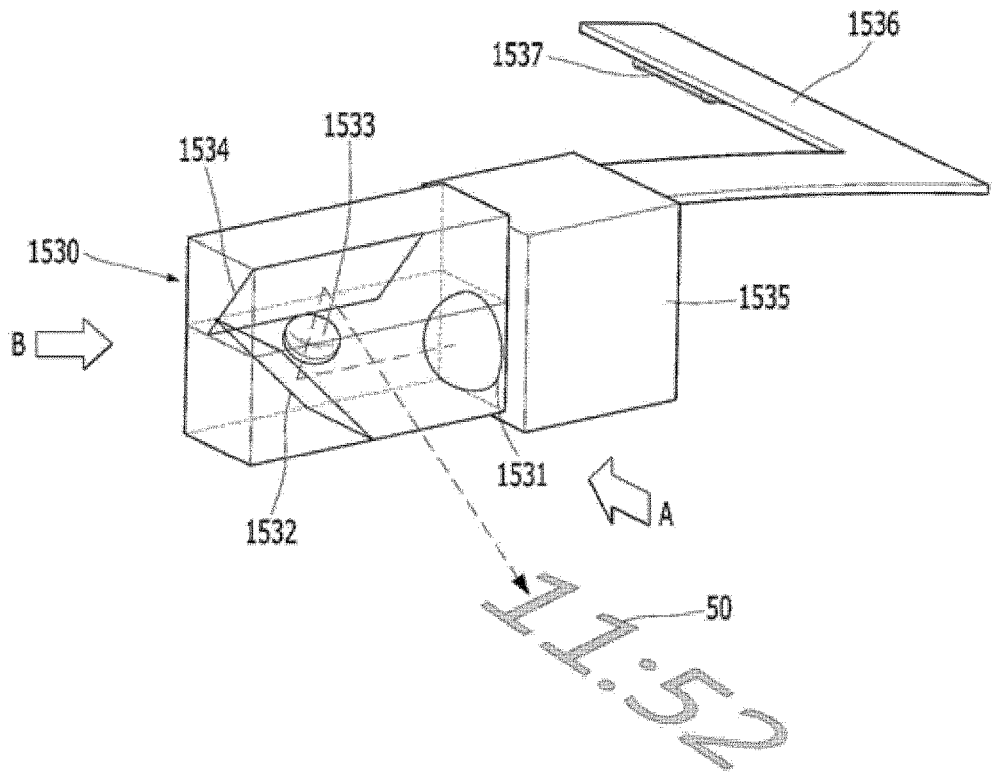
FIG. 6 is a view illustrating a projector module of a wearable device according to the present invention.

The projector 1535 coupled to the first frame 106 projects the image 50 toward the wrist or hand of the user. FIG. 6 is a view illustrating a projector module 153 of a wearable device 100 according to the present invention.

The projector module 153 includes the projector 1535 for outputting the image 50 along an image signal, and a lens module 1530 for shooting out the image projected from the projector 1535 by adjusting a direction and a size of the image. The projector 1535 is an optical device for projecting an image on a screen in accordance with an image signal. The image projected from the projector 1535 and then displayed on the screen is varied depending on a distance, position and angle from the screen.

If the projector is arranged in a direction (insertion direction of wrist) in which the opening 105 is formed to display an image on the wrist or hand of the user, the projector 1535 and the lens module 1530 are arranged in parallel, whereby a problem occurs in that a width of a ring is increased.

To solve the problem, according to the present invention, the projector 1535 is arranged to display an image in a direction orthogonal to the direction of the opening 105 of the ring, that is, a tangent direction of the ring, and the lens module 1530 is provided with reflective plates 1532 and 1534 to change a direction of light, thereby displaying the image 50 toward the hand of the user.

As shown in FIG. 6, the lens module 1530 may include two reflective plates 1532 and 1534. That is, the lens module 1530 may include a first reflective plate 1532 for reflecting the image incident from the projector 1535 arranged in a lateral direction toward the outside of the ring and a second reflective plate 1534 for again reflecting the reflected image toward the hand of the user.

Figure 7:
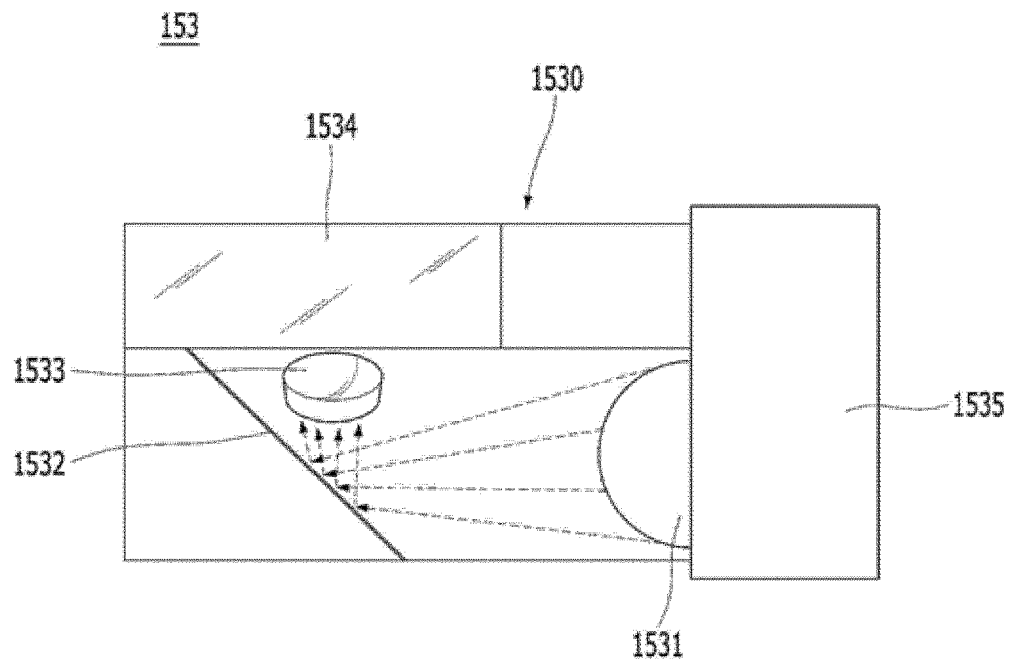
FIG. 7 is a front view viewed from A of FIG. 6.

FIG. 7 is a front view viewed from A of FIG. 6, and illustrates that the image projected from the projector 1535 is reflected by the first reflective plate 1532 and headed toward the second reflective plate 1534. The first reflective plate 1532 is inclined toward the outside (upper side in the drawing) of the ring from a viewing direction of the projector 1535 to reflect the image projected from the projector 1535 toward the second reflective plate 1534 arranged at the outside.

Figure 8:
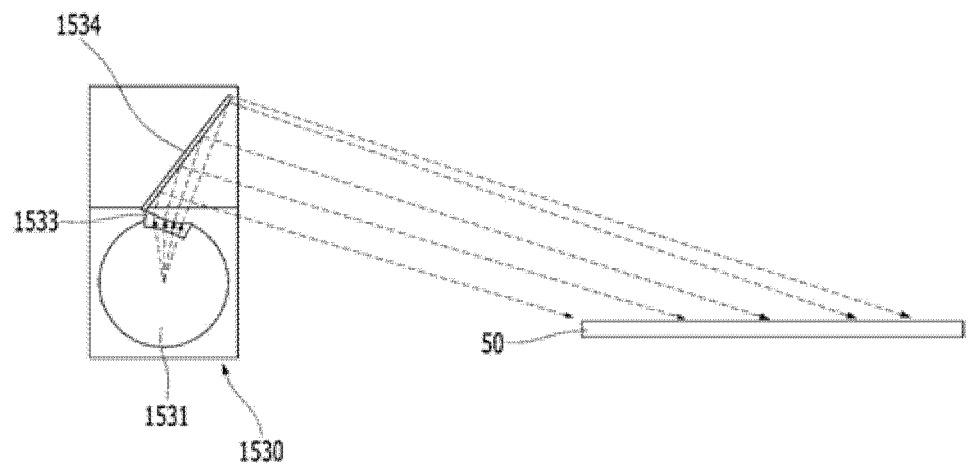
FIGS. 8 and 9 are side views viewed from B of FIG. 6.
Figure 9:
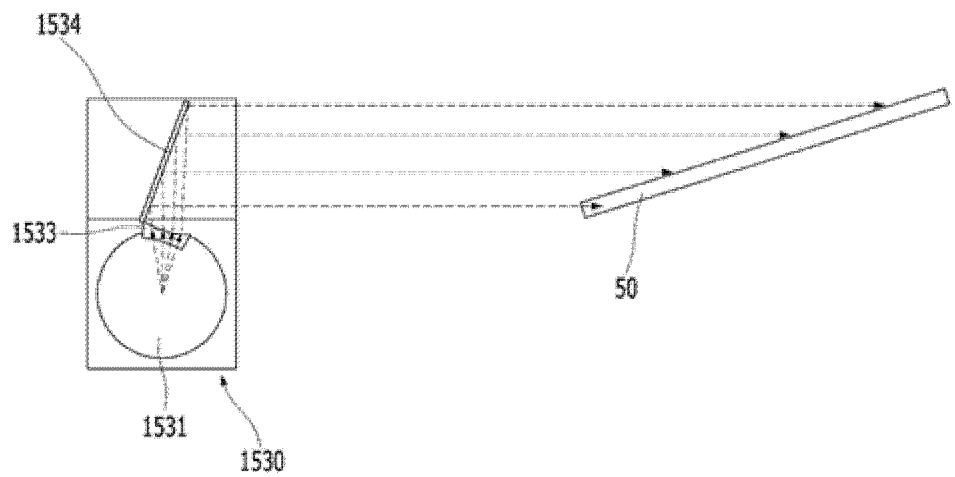

FIGS. 8 and 9 are side views viewed from B of FIG. 6, and illustrate that the image reflected by the first reflective plate 1532 is reflected by the second reflective plate 1534 and then output to the hand of the user. The second reflective plate 1534 is inclined toward the hand of the user from a central direction (lower side in the drawing) of the ring to reflect the image reflected by the first reflective plate 1532 toward the hand of the user.

Since the image projected from the projector 1535 is widely spread by diffusion of light, the image is delivered to the first reflective plate 1532 of a small size by passing through a first lens 1531 for collecting light. That is, a convex lens may be used as the first lens 1531.

As the light reflected by the first reflective plate 1532 is reflected by the second reflective plate 1534, its direction is changed, whereby the light is projected toward the hand or wrist of the user. At this time, a second lens 1533 for magnifying the image reflected by the first reflective plate 1532 may be interposed between the first reflective plate 1532 and the second reflective plate 1534 to obtain a large sized image. That is, a concave lens may be used as the second lens 1533. Since the image projected from the projector 1535 is reflected twice, the image may be provided to the user without change of its left and right image.

The light projected from the projector module 153 is projected on the hand of the user, and the image projected on the hand of the user is spread by the second lens 1533, whereby the image becomes greater if a distance from the screen on which the image is displayed becomes far away. Therefore, since the image corresponding to a portion close to the projector module 153 is displayed at a size smaller than that of the image corresponding to a portion far away from the projector module 153, in order to counterbalance the difference, the magnification of the image projected from the projector 1535 may be varied. The image projected toward the portion close to the projector module 153, that is, the portion close to the wrist may be changed at a greater size, whereas the image projected toward the portion far away from the wrist may be changed at a smaller size.

If the user always maintains the wrist at a uniform angle, an angle between the projector 1535 and the hand of the user may always be maintained uniformly. However, if the user bends his/her wrist to allow the angle to be changed, an angle between a surface (the back of the user's hand) toward which the image 50 is projected and the projector module 153 is varied, whereby a problem occurs in that the image 50 is distorted or an exact image is not displayed.

In this respect, the wearable device 100 of the present invention may sense a bent level of the wrist by using a proximity sensor 141, a myoelectric sensor 142, etc. The proximity sensor 141 may calculate a distance with a proximate object as well as discover the presence of the proximate object. A signal is projected on two or more positions, whereby an angle with the hand of the user is calculated using the time required to allow the signal to be reflected and recovered, and then an angle of the wrist is calculated.

Alternatively, the myoelectric sensor 142 senses a fine myoelectric change occurring when the user moves his/her wrist muscle, thereby identifying which muscle has moved and calculating a bent angle of the wrist through movement of the corresponding muscle.

The bent level of the wrist, that is, an angle between the hand and the wrist may be calculated based on data sensed by the sensor 140, and the lens module 1530 may be rotated in response to the angle, or an angle of the second reflective plate 1534 may be adjusted as shown in FIG. 9, whereby an exact image may be projected on the hand of the user.

It is possible to project the image 50, which is not distorted, on the hand of the user by adjusting a rate of the image projected from the projector 1535 as well as rotating the lens module 1530 or adjusting the angle of the second reflective plate 1534.

Figure 10:
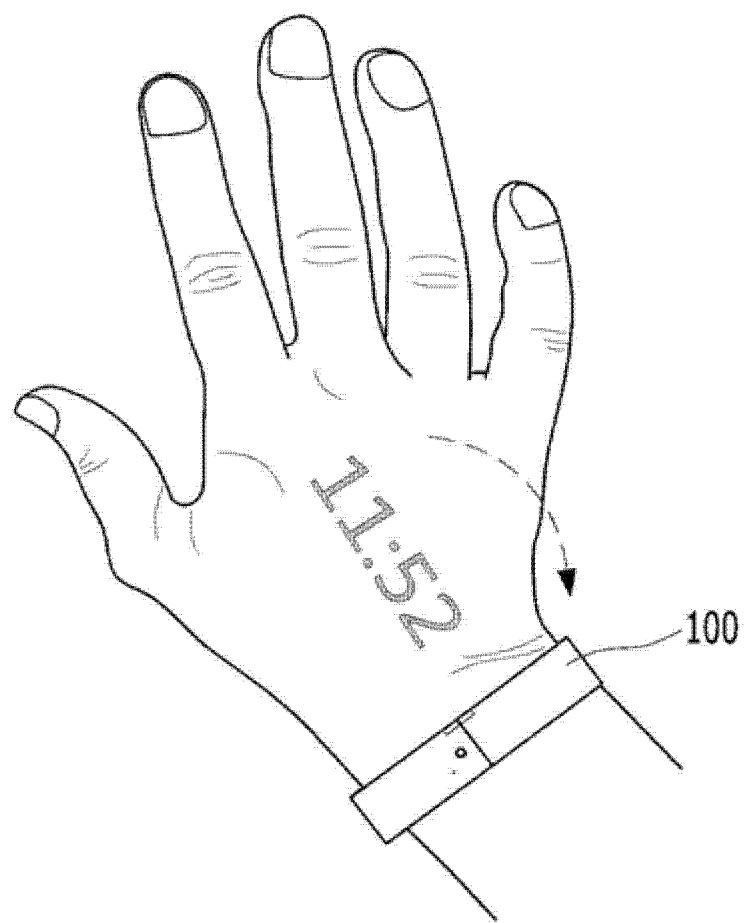
FIG. 10 is a view illustrating a screen change based on wrist movement of a wearable device according to the present invention.

FIG. 10 is a view illustrating a screen change based on wrist movement of a wearable device 100 according to the present invention. The wearable device 100 of the present invention may control the image output from the projector 1535 in accordance with movement of the wrist. Examples of movement of the wrist may include a bent direction of the wrist (toward the back of the hand or palm), a twist direction of the wrist (clockwise or counterclockwise), and the number of bent times, and a command may be identified by the examples of movement of the wrist. Furthermore, the command may be input by sensing of movement of fingers. For example, if the user bends his/her wrist one time, a clock screen may be switched to a calendar screen.

The user may input a command related to the projected image as well as simply switch the projected image. For example, if the user bends his/her wrist toward the palm, the operation of the projector module 153 may be stopped. If a call signal is received, the projector module 153 is operated to notify the user of a received call. The user may receive or hang up a call depending on a bent direction of the wrist.

If the state that the user's wrist is bent continues to be maintained, the lens module 1530 may change a direction toward which the image is projected or the projector 1535 may adjust the image. If instantaneous movement is sensed, it may be recognized as a user command, whereby screen switching and function corresponding to the sensed movement may be performed.

Figure 11:
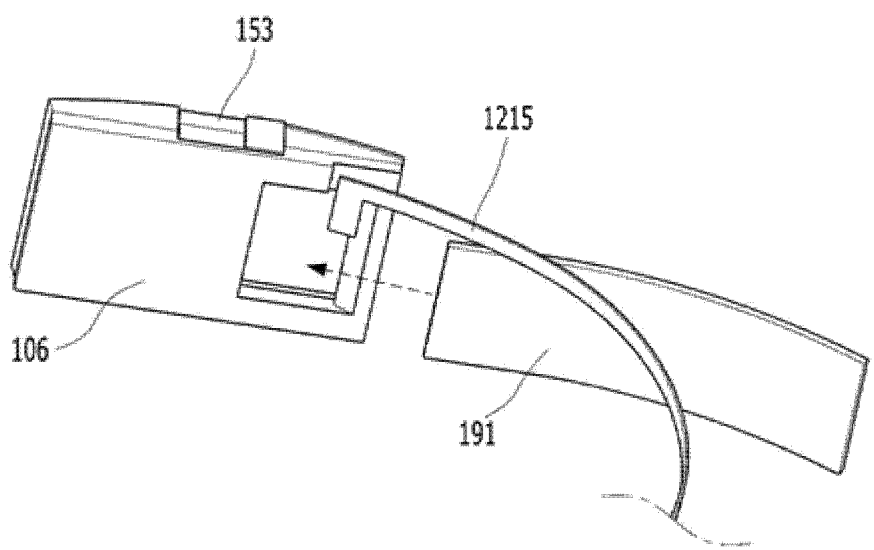
FIG. 11 is a view illustrating a first frame and a battery of a wearable device according to the present invention.

FIG. 10 is a view illustrating a first frame 106 and a battery 191 of a wearable device 100 according to the present invention, and FIG. 11 is a cross-sectional view illustrating a first frame 106 and a battery 191 of a wearable device 100 according to the present invention.

Since the battery 191 of the present invention should be packaged in the ring shaped cases 101 and 102 including a curve, a curved battery 191 may be used. One end of the curved battery 101 is inserted to the first frame 106 and then connected to the main board 185 and supplies a power to each part. The portion of the frame 106 or 107 to which the battery 191 is inserted may form a curve as shown in FIG. 11.

Figure 13:
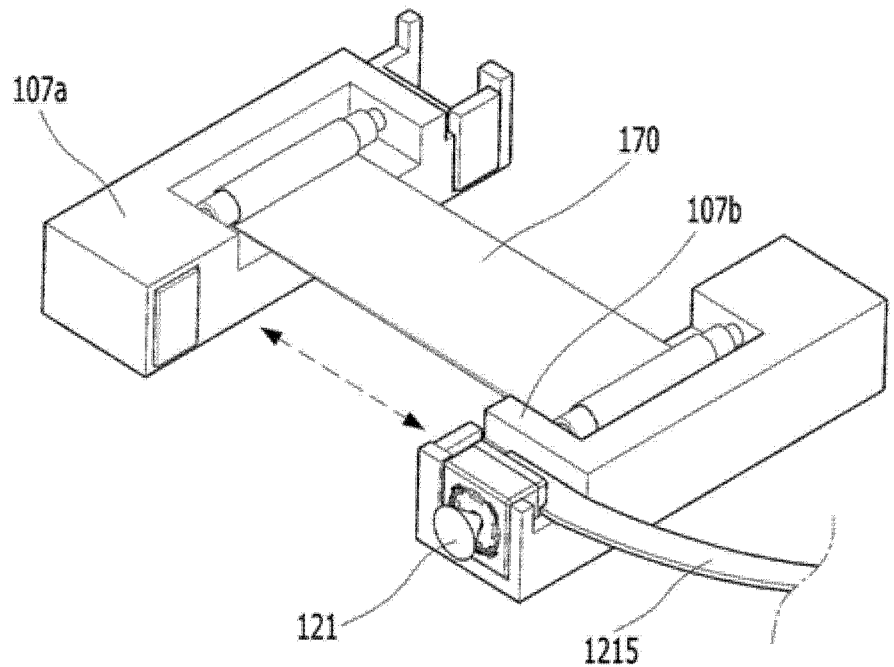
FIG. 13 is a perspective view illustrating a second frame portion of a wearable device according to the present invention.

FIG. 13 is a perspective view illustrating a second frame 107 portion of a wearable device 100 according to the present invention. Referring to FIG. 5, the second frame 107 is spaced apart from the first frame 106 and a camera is arranged in the second frame 107. The flexible substrate 1215 for connecting the camera with the main board 185 is arranged between the first frame 106 and the second frame 107.

The camera may be headed for the same direction as the direction for which the projector module 153 is headed, may be arranged toward the outside of the ring, or may be rotated to change a photographing direction.

Figure 12:
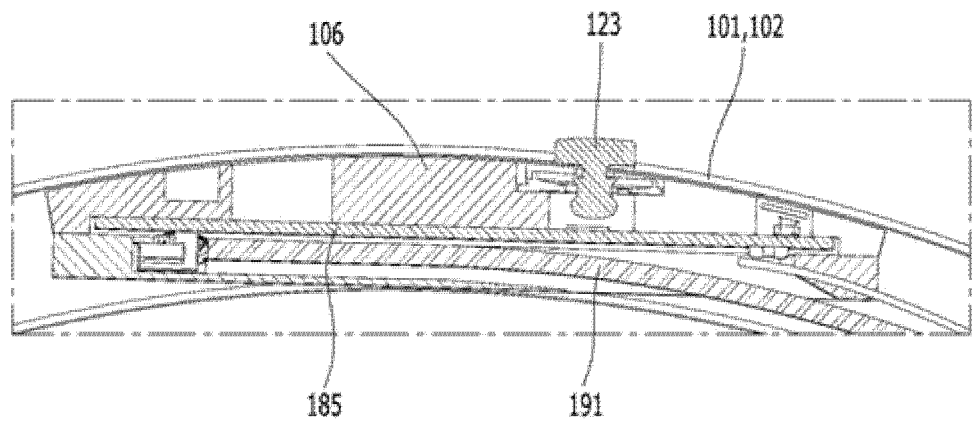
FIG. 12 is a cross-sectional view illustrating a first frame and a battery of a wearable device according to the present invention.

The second frame 107 may include an elastic member 170 to allow a user to easily wear the wearable device by adjusting a length of the ring shaped wearable device 100 in addition to the camera. As shown in FIG. 12, if the user pulls the cases 101 and 102 at both sides of the elastic member 170 in a tangent direction of the ring, the length of the elastic member 170 is increased and at the same time the length of the ring is increased.

At this time, if the cases 101 and 102 are all made of a hard material, since the cases 101 and 102 are not increased, the cases 101 and 102 are partially made of a soft material. A shape of the case made of a soft material is changed, whereby the size of the ring may be increased.

The above detailed description is to be considered in all respects as illustrative and not restrictive. The scope of the present invention should be determined by reasonable interpretation of the appended claims and all changes which come within the equivalent scope of the invention are included in the scope of the invention.

The invention claimed is:

1. A wearable device comprising:
   a case having a ring shape, the ring shape of the case defining an opening at a center of the case, the opening being configured to receive a wrist of a user;
   a projector located in the case, the projector being configured to output an image toward a hand of the user when the wrist of the user is located in the opening of the case;
   a sensor located in the case, the sensor being configured to sense a bent angle of the user's wrist;
   a lens module configured to:
   receive the image from the projector at a side of the lens module;
   adjust a direction of the image;
   adjust a size of the image; and
   project the image at a front of the lens module; and
   a controller configured to control the projector and the lens module in accordance with the bent angle of the user's wrist,
   wherein the lens module includes:
   a first reflective plate configured to receive the image incident at the side of the lens module and to reflect the image in a radial direction of the ring shape of the case,
   a second reflective plate configured to receive the image reflected by the first reflective plate and to reflect the image in an axial direction of the ring shape of the case,
   a first lens configured to reduce a size of the image incident at the size of the lens module, and to deliver the image to the first reflective plate, and
   a second lens located between the first reflective plate and the second reflective plate, the second lens being configured to magnify the image reflected by the first reflective plate, and to deliver the image to the second reflective plate.

2. The wearable device according to claim 1, wherein the controller is configured to control the image output from the projector to reduce distortion of the image displayed on the hand of the user by separately adjusting a size of an image displayed on a portion of the hand of the user that is relatively close to the user's wrist and a size of an image displayed on a portion of the hand of the user that is relatively far away from the user's wrist.

3. The wearable device according to claim 1, wherein the controller is configured to adjust the direction and the size of the image projected by the lens module according to the bent angle of the user's wrist.

4. The wearable device according to claim 1, wherein the controller is configured to change the image output from the projector according to the bent angle of the user's wrist.

5. The wearable device according to claim 1, wherein the controller is configured to adjust an inclination angle of the second reflective plate.

6. The wearable device according to claim 1, wherein at least a portion of the case comprises a flexible material, and
wherein the wearable device further comprises an elastic member located at one side of the case, the elastic member being spaced apart from the projector, the elastic member being configured to adjust a size of the ring shape of the case in accordance with a variable length of the elastic member.

7. The wearable device according to claim 1, further comprising:
a frame on which the projector is mounted;
a main board fixed to the frame;
a camera spaced apart from the projector; and
a flexible substrate connecting the camera with the main board.

8. The wearable device according to claim 7, further comprising a battery located in the case, the battery having a curved shape, the battery having one side located adjacent to the frame,
wherein the frame further includes a battery holder having a curved shape corresponding to the curved shape of the battery.

9. The wearable device according to claim 1, further comprising a wireless communication unit located in the case, the wireless communication unit being configured to receive an image signal from an external terminal.

10. The wearable device according to claim 1, further comprising:
a frame on which the projector is mounted;
a main board fixed to the frame; and
a camera spaced apart from the projector.

11. The wearable device according to claim 10, further comprising:
a battery located in the case, the battery having a curved shape, the battery having one side located adjacent to the frame; and
a battery holder having a curved shape corresponding to the curved shape of the battery,
wherein the controller is configured to adjust a direction and a size of the image projected by the lens module according to the bent angle of the user's wrist.

12. A wearable device comprising:
a case having a ring shape, the ring shape of the case defining an opening at the center of the case, the opening being configured to receive a wrist of a user;
a projector located in the case, the projector being configured to output an image toward a hand of the user when the wrist of the user is located in the opening of the case;
a lens module adjusting a direction and a size of the image;
a sensor for sensing a bent angle of the user's wrist; and
a controller configured to control the projector and the lens module in accordance with the bent angle of the user's wrist,
wherein the lens module includes:
a first reflective plate configured to receive the image incident at a side of the lens module and to reflect the image in a radial direction of the ring shape of the case,
a second reflective plate configured to receive the image reflected by the first reflective plate and to reflect the image in an axial direction of the ring shape of the case,
a first lens configured to reduce a size of the image incident at the side of the lens module, and to deliver the image to the first reflective plate, and
a second lens located between the first reflective plate and the second reflective plate, the second lens being configured to magnify the image reflected by the first reflective plate, and to deliver the image to the second reflective plate.

13. The wearable device according to claim 12, wherein the controller controls the image projected from the projector to reduce distortion of the image displayed on the hand of the user by separately adjusting a size of an image displayed on a portion close to the user's wrist and a size of an image displayed on a portion far away from the user's wrist.

14. The wearable device according to claim 12, wherein the controller adjusts a direction and size of the image projected by the lens module, in accordance with the bent angle of the user's wrist.

15. The wearable device according to claim 12, wherein the controller is configured to change the image output from the projector in accordance with the bent angle of the user's wrist.

16. The wearable device according to claim 12, wherein the sensor is at least one of a myoelectric sensor and a proximity sensor.

* * * * *